United States Patent [19]

Levings et al.

[11] Patent Number: 5,087,693
[45] Date of Patent: Feb. 11, 1992

[54] BOVINE MONOCLONAL ANTIBODIES TO BOVINE HERPESVIRUS I FROM SEQUENTIAL FUSION HETEROHYBRODIMAS

[75] Inventors: Randall L. Levings, Ames; Ione R. Stoll, Story City, both of Iowa

[73] Assignee: The United States of America as represented by the Secretary of Agriculture, Washington, D.C.

[21] Appl. No.: 689,572

[22] Filed: Apr. 23, 1991

Related U.S. Application Data

[62] Division of Ser. No. 271,825, Nov. 16, 1988, Pat. No. 5,026,646.

[51] Int. Cl.$^5$ .............................................. C07K 15/28
[52] U.S. Cl. ...................... 530/387; 530/808; 935/104
[58] Field of Search .................. 530/387, 808; 935/104

Primary Examiner—Esther L. Kepplinger
Assistant Examiner—Susan L. Futrovsky
Attorney, Agent, or Firm—M. Howard Silverstein; John D. Fado; Curtis P. Ribando

[57] ABSTRACT

Stable heterohybridomas which secrete monoclonal antibodies to bovine herpesvirus-1 (BHV-1) are obtained by fusing primed bovine lymphocytes with an immortal cell line, selecting for secretial hybrids, and sequentially re-fusing such hybrids with fresh bovine lymphocytes. Three such heterohybridomas which secrete neutralizing antibody to BHV-1 have been obtained in this manner and have been deposited in the ATCC as Accession Nos. HB9907, HB9908, and HB9909. The neutralizing antibodies are useful in immunological research, pathological diagnosis, and therapeutic disease control. Specifically, they have utility as serologic control regents in assays, and as primary reagents in anti-species, anti-isotype, and anti-idiotypic antibody production.

2 Claims, No Drawings

BOVINE MONOCLONAL ANTIBODIES TO BOVINE HERPESVIRUS I FROM SEQUENTIAL FUSION HETEROHYBRODIMAS

This is a division of application Ser. No. 07/271,825, filed Nov. 16, 1988 now U.S. Pat. No. 5,026,646.

BACKGROUND OF THE INVENTION

1. Field of the Invention

This invention relates to a novel class of bovine-murine hybridomas which produce neutralizing monoclonal antibodies to bovine herpesvirus-1 (BHV-1). BHV-1 is the agent responsible for infectious pustular vulvovaginitis and bovine rhinotracheitis. Secondary infections associated with rhinotracheitis may develop into an economically devastating disease known as "shipping fever." Efforts to control diseases induced by BHV-1 have been hindered for want of reliable diagnostic reagents and effective therapeutic agents.

2. Description of the Prior Art

Attenuated vaccines which have been developed against BHV-1 are typically characterized by undesirable side effects, and the killed vaccines are largely ineffective. Lupton et al. [Am. J. Vet. Res. 41:383 (1980)] have reported on a crude subunit vaccine for protecting calves against the infection and shed of infectious BHV-1. Van Drunen et al. [J. Virol. 59:401 (1980)] and Babiuk et al. [Virology 159:57 (1987)] have shown that the administration of each of three major envelope glycoproteins of BHV-1 to calves will protect against combined challenge with BHV-1 and *Pasteurella haemolytica*, but not against viral replication and shedding. Passively administered, murine, monoclonal antibodies specific for epitopes on the three envelope glycoproteins were found by Marshall et al. to be nonprotective against BHV-1 infection in calves.

Presumably, monoclonal antibody of bovine origin would have advantages in many applications, including: the determination of key epitopes responded to by the host; cooperation between antibody and host accessory immunologic cells; repeated prophylactic or therapeutic administration of antibodies to the host; production of some types of anti-idiotypic antibodies; and as control reagents for serologic assays. For example, Srikumaran et al. [Abstract of Papers, 67th Annual Meeting of the Conference of Research Workers in Animal Disease, 86: Abstr. No. 143 (1986)] fused lymph cells from a calf immunized against infectious bovine rhinotracheitis virus (IBRV) with the nonsecreting cell line SP2/0. Two of the recovered hybridomas secreted nonneutralizing, bovine monoclonal antibodies that reacted with IBRV in both indirect solid-phase radioimmunodiffusion assay (RIA), and indirect fluorescent antibody assay (IFA). Tucker et al. [Hybridoma 3(2):171 (1984)] demonstrated that antibody secretion vigor of interspecies hybridomas could be enhanced by re-fusing a chemically selected mouse/calf hybridoma with immunized calf lymph node cells. In contrast to the original mouse/calf fusion products which failed to maintain antibody secretion in culture, the re-fused lines carried two to three times the number of bovine chromosomes as the single-fused hybridoma and maintained active antibody secretion over a 5-month period.

SUMMARY OF THE INVENTION

We have now discovered that by fusing bovine lymphocytes with cells from an immortal cell line and then sequentially re-fusing the resultant heterohybridomas which have been selected for secretion of monoclonal antibody to BHV-1, stable lines can be obtained for producing neutralizing antibody to the virus. Specifically, three such lines have been obtained from a triple fusion sequence. In the first fusion of the series, lymph node cells from a calf hyperimmunized with BHV-1 were fused with the nonsecretor murine hybridoma SP2/0, and first-generation monoclonal antibody-producing, bovine x murine, heterohybridomas were selected. These first-generation heterohybridomas were then re-fused with primed lymph node cells similar to those used in the first fusion, and second-generation monoclonal antibody-producing, bovine[2] x murine, heterohybridomas were selected. Finally, the second-generation heterohybridomas were fused with primed lymph node cells and a third generation of bovine[3] x murine heterohybridomas were selected. Of the resultant triple fusion products which were found to be stable, approximately 4% were sufficiently bovine in nature so as to secrete IgG1 antibodies which specifically neutralized BHV-1 in vitro without complement.

In accordance with this discovery it is an object of this invention to provide a method, using re-fusion technology, for obtaining stable, continuously proliferating, hybrid cell lines capable of producing neutralizing antibodies to BHV-1.

It is also an object of the invention to provide three specific bovine[3] x murine heterohybridomas for producing neutralizing antibodies to BHV-1.

Another object of the invention is to provide a source for bovine antibodies to BHV-1 which offer unique advantages over host polycolonal antiserum or murine monoclonal antibodies in immunological research, pathological diagnosis, and therapeutic disease control.

A specific object of the invention is to produce bovine monoclonal antibodies which have utility as serologic control reagents in assays, and as primary reagents in anti-species, anti-isotype, and especially anti-idiotypic antibody production.

Other objects and advantages of the invention will become readily apparent from the ensuing description.

DETAILED DESCRIPTION OF THE INVENTION

Establishing the antibody-secreting cell lines for use in the invention is a multistep procedure which includes hyperimmunizing a bovine animal to induce a proliferation of antibody-producing cells, promoting fusion between the primed bovine cells and cells of an immortal cell line, selecting for antibody-secreting heterohybridomas, screening the hybridomas for selectability in a subsequent fusion stage, and then sequentially re-fusing the selected hybridomas with fresh, primed bovine cells to enrich the bovineness of the recovered cell lines. The objective is to produce cell lines which are continuous (i.e., immortal) and stable. The term "stable" is used herein to describe the property of continuously producing antibody.

The immortal cell line may be of any origin as known in the art but is most desirably one which does not itself secrete antibody. Immortal cell lines most commonly used in fusion technology are of murine origin, especially those which are hypoxanthine-guanine, phosphoribosyl transferase (HGPRT) negative. Particularly preferred for use herein is the SP2/0 myeloma established from a BALB/c mouse by Shulman et al. [Nature 276: 269–270 (Nov. 16, 1978)]. An objective of the fusion procedure is to maximize the number of myeloma cells by passaging the line on a suitable growth medium according to a schedule allowing for the log phase to coincide with the fusion date. The cell line is also passaged two or three times at 4- to 8-week intervals on a growth medium containing 6-thioguanine and 8-azaguanine or the like for the purpose of maintaining susceptibility to a screening agent during the hybridoma selection, as described in further detail below.

Bovine cells for use in the fusion are HGPRT-positive lymphocytes which have been primed for antibody production to BHV-1 by hyperimmunization of an animal with BHV-1 antigen. Lymph node cells of a calf are a suitable source for these lymphocytes, and they are most optimally primed by injection of the BHV-1 antigen directly into the region of the node itself. Live, low passage BHV-1 in a suitable adjuvant is an effective antigen for this purpose. Of course, it would be understood by a person in the art that the purer the antigenic material used for the hyperimmunization, the more specific the lymphocytic response and the more facile the subsequent hybridoma selection process.

It is theorized that there is a certain advantage to using primed lymphocytes from the same individual animal for each of the sequential re-fusions. Lymphocytes from the same animal have similar histocompatibility antigens. This approach will hereafter be referred to as "selfing." For selfing to be implemented, the cells either have to be nonsacrificially recovered from the animal prior to each fusion, or else they have to be recovered at one time and maintained in the primed state such as by cryogenic preservation or in culture.

The preferred immunization regimen for effective priming of lymph node cells is initiated by subcutaneous injection of the antigen, emulsified in an adjuvant, in the area drained by the target superficial lymph node at 2-3 week intervals. At 3-4 days before the fusion, unadjuvanted virus is again injected into the area. The initial inoculation stimulates the lymphocytes to produce the anti-BHV-1 antibodies, and the subsequent injection(s) stimulates further cell multiplication. Immunizing 3-4 days before fusion maximizes the number of lymphocytes in metaphase. Determination of the optimum dose of antigen would be within the skill of a person in the art, though 5 ml of $10^5$ pfu per injection has proven to be effective.

On the day of fusion, the lymphocytes are harvested and cosuspended in a suitable growth medium with the cells from the immortal cell line, hereafter referred to as the "myeloma cells." The preferred lymph node:-myeloma cell ratio is in the range of about 1:1 to 1:2. Standard polyethylene glycol (PEG) fusion procedures such as those reported by Van Deusen et al. [Am. Assoc. Vet. Lab. Diagnost., 24th Annual Proc. 211–228 (1981), herein incorporated by reference] or modifications thereof may be employed.

The primary cells recovered from the fusion process are plated in a selective medium containing a screening agent against unfused myeloma cells and myeloma×-myeloma fusions. Conventional media for this purpose are HMT (hypoxanthine, methotrexate, and thymidine) or HAT (hypoxanthine, aminopterin, and thymidine) in which the methotrexate or aminopterin functions as the screening agent in that it kills the susceptible myeloma cells. The unfused lymphocyte cells and bovine x bovine fusions will cease to proliferate after about 1 or 2 week's time. In a normal workup, the cells in the selective medium are cultured at about 37° C. in a $CO_2$-enriched atmosphere at high humidity. Medium is periodically screened for antibody production and replenished as necessary. Applicable screening tests for hybridoma selection include IFA, RIA, immunoelectrophoresis, enzyme-linked immunosorbent assay (ELISA), and indirect ELISA. The selected primary (1°) hybrids may be serially passaged into larger wells or into flasks as cell numbers increase.

If the hybrids appear not to be stable in terms of antibody production, they are screened for selectability in a subsequent fusion stage to be performed. This is accomplished by cultivating the hybrids until a suitable number of cells revert to a condition of being sensitive to one of the screening agents referred to above. The screening agent-sensitive cells are then selected with a second agent which destroys the cells resistant to the first screening agent. For example, if the primary cells from the first fusion were selected for methotrexate resistance, they could be cultivated until a predetermined population reverted to methotrexate sensitivity. The methotrexate-resistant cells are conveniently eliminated by cultivation in the presence of 6-thioguanine, thereby leaving the methotrexate-sensitive cells available for the next stage of fusion and primary cell selection.

The nonsecreting bovine x myeloma cells carried forward from the first fusion stage described above are subjected to a "re-fusion" with fresh, primed lymphocytes as previously discussed. The fusion products are cultivated in a selection medium, and the bovine x bovine x murine (bovine$^2$ x murine) hybrids are periodically assayed for antibody production in the same manner as the bovine x murine hybrids. The screening for subsequent selectability and the re-fusion processes are repeated as necessary until a stable heterohybidoma is identified. The repeated "back-crossing" serves to increase the degree of bovineness of the fusion product which is ultimately recovered. Based upon the observations of Tucker et al., supra, this phenomenon is believed to be due to an increased number of bovine chromosomes introduced by virtue of each re-fusion.

The 1° hybrids from the final stage of re-fusion are cloned to insure that all progeny secrete the desired antibody. Cloning is accomplished by plating or otherwise propagating individual cells selected from the chosen hybridomas. It is conventional for the cloned cultures to be sequentially recloned two or more times to insure homogeneity of the cell line and for expansion of the culture. For antibody production, the cloned cells are cultured in vitro in a suitable growth medium, and the antibody is recovered from the supernatant fluid.

The following example are intended only to further illustrate the invention and is not intended to limit the scope of the invention which is defined by the claims.

EXAMPLE 1

Immunizations

A subadult Holstein breed bovine was subcutaneously injected with 5 ml of live, low passage BHV-1 $10^5$ pfu/ml emulsified with equal volumes of Incomplete Freunds Adjuvant in the area drained by the target superficial lymph node at 2-3 week intervals. At 3-4 days before fusion, unadjuvanted virus was injected in the area. The right prescapular, left prescapular, and right prefemoral superficial lymph nodes were sequentially targeted for the first, second, and third fusions, surgically removed under general anesthesia.

Fusions and Cell Culture

Lymph nodes were sectioned and passed through an 80-mesh sieve (cell sorter). The extracted cells were washed and then frozen or immediately used for fusion. Fusions were performed by a modification of a standard PEG protocol [Van Deusen et al., supra] using myeloma cell:lymph node cell ratios of approximately 1, seeded into 96 well plates. All plate cultures were fed with 1:1 Dulbecco's minimal essential medium (DMEM) and high glucose with 10% horse serum to conditioned media from fusion partner cultures appropriate to each fusion. All useful primary cultures were cloned and subcloned by limiting dilution using an automatic micropipettor and were controlled-rate frozen in liquid nitrogen. Fusion partner selection for methotrexate sensitivity was achieved by passage in media containing 6-thioguanine and 8-azaguanine.

The first fusion of SP2/0 murine myeloma cells with the right prescapular calf lymph nodes cells in a 3:1 mixture, respectively, resulted in two transiently bovine Ig secreting primary cell lines ($\alpha$BL5-1.Y1B1 and $\alpha$BL5-1.Y3E6). After their secretion ceased, the lines were selected for methotrexate sensitivity by passage in media containing 6-thioguanine and 8-azaguanine. The two methotrexate-sensitive bovine:murine heterohybridomas were combined in a 1:1 ratio and mixed with lymph node cells from the immunized and extracted left prescapular lymph node from the same calf used previously in a 1:1 ratio. This fusion again resulted in two transiently bovine Ig secreting cell lines ($\alpha$BL5A1-.Y2C2, and $\alpha$BL5A1.Y5A11). After the secretion ceased, the lines were selected for methotrexate sensitivity as before. Cells from the two methotrexate-sensitive bovine$^2$ x murine heterohybridomas were combined in a 1:1 ratio and fused with fresh lymph node cells from an immunized, right prefemoral lymph node from the same calf as before, this time from a 1:2 mixture, respectively. The fusion resulted in 160 bovine$^3$ x murine primary heterohybridomas secreting bovine antibodies reacting strongly in indirect fluorescent antibody tests using BHV-1. Sixty-eight of these heterohybridomas were stable and recoverable. Three bovine$^3$ x murine heterohybridomas secreted virus neutralizing, bovine IgG1 antibodies as determined by immunoelectrophoresis. These hybridomas were cloned and subcloned. The subclones are maintained as cell lines $\alpha$BL5C2.870005, $\alpha$BL5C2.870009, and $\alpha$BL5C2.870016 at the National Veterinary Services Laboratories in Ames, IA, and have been deposited under the Budapest Treaty in the American Type Culture Collection in Rockville, MD, and assigned Accession No. ATCC HB 9907, ATCC HB 9908, and ATCC HB 9909, respectively. The molecular weights of the heavy and light chains of the antibody produced by 870009 are 49 Kd and 26 Kd, respectively, as determined by precipitation PAGE (polyacrylamide gel electrophoresis). For the antibody from 870016, the molecular weights are 50 Kd and 25 Kd, respectively. The chain weights of 870005 have not been determined but are expected to be about the same as those of 870009 and 870016.

In parallel with the final fusion sequence described above, fresh lymphocytes were also fused with: 1) SP2/0 myeloma cells; and 2) the combined $\alpha$BL5-1.Y1B1 and $\alpha$BLB-1.Y3E6 bovine x murine hybridomas. The yields of secretial primary hybrids and stable cell lines for the resultant bovine x murine and bovine$^2$ x murine fusions were compared to those for the bovine$^3$ x murine fusions. It is apparent from the results summarized in Table I, below, that the success rate for obtaining a stable secreter of bovine monoclonal antibody by triple fusion (bovine$^3$ x murine) is approximately 10-fold that of either single or double fusions.

TABLE I

| Fusion | No. of secretial hybrids | No. of stable hyrbids |
|---|---|---|
| 1st (B$^1$ × M)$^a$ | 7 | 7 |
| 2nd (B$^a$ × M)$^b$ | 4 | 3 |
| 3rd (B$^3$ × M)$^c$ | 160 | 68 |

$^a$Conducted in eight 96-well plates.
$^b$Conducted in eleven 96-well plates.
$^c$Conducted in ten 96-well plates.

EXAMPLE 2

At approximately 6 days of age, New Zealand White Rabbits were injected by the intracardiac route with 1 ml of antibody fluid. Antibody fluid included concentrated tissue culture supernatant from each of the three heterohybridoma subclones obtained in Example 1, similarly treated media controls, anti-BHV-1 bovine antiserum, and fetal bovine serum. Twenty-four hours later, the rabbits were challenged by intracardiac injection with 1 ml fluid containing approximately 10$^7$ pfu of BHV-1. Deaths observed in 3–14 days were considered specific, and protection is defined as a reduction in mortality of 50%. The results are reported in Table II, below. The differences observed between the percent mortality for bovine antiserum and the percent mortality for each of the monoclonal antibodies is presumed to be attributed to the higher neutralization titers of the polyclonal antiserum.

TABLE II

| Reduction in BHV-1 Specific Rabbit Mortality by Bovine Antibody | | |
|---|---|---|
| Antibody treatment | Deaths/No. treated | % Mortality |
| none | 45/48 | 93.8 |
| media control | 18/22 | 81.8 |
| 870005 | 1/8 | 12.5 |
| 870009 | 4/12 | 33.3 |
| 870016 | 1/14 | 7.1 |
| fetal bovine serum | 10/17 | 58.8 |
| bovine antiserum | 2/39 | 5.1 |

We claim:
1. A neutralizing and protective monoclonal antibody to bovine herpesvirus-1.
2. A neutralizing monoclonal antibody as described in claim 1 produced by a heterohybridoma selected from the group consisting of $\alpha$BL5C2.870005 (ATCC H 9907), $\alpha$BL5C2.870009 (ATCC HB 9908), and $\alpha$BL5C2.870016 (ATCC HB 9909).

* * * * *